US007094570B2

(12) United States Patent
Renauld et al.

(10) Patent No.: US 7,094,570 B2
(45) Date of Patent: Aug. 22, 2006

(54) ISOLATED NUCLEIC ACID MOLECULES WHICH ENCODE A SOLUBLE IL-TIF/IL-22 RECEPTOR OR BINDING PROTEIN WHICH BINDS TO IL-TIF/IL-22, AND USES THEREOF

(75) Inventors: Jean-Christophe Renauld, Brussels (BE); Laura Dumoutier, Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 10/385,586

(22) Filed: Mar. 11, 2003

(65) Prior Publication Data

US 2004/0180399 A1 Sep. 16, 2004

(51) Int. Cl.
*C12P 21/06* (2006.01)

(52) U.S. Cl. ............... 435/69.1; 435/320.1; 435/252.3; 435/325; 536/23.5; 530/350; 530/351

(58) Field of Classification Search ............... 435/69.1, 435/320.1, 252.3, 325, 6; 536/23.5; 530/350
See application file for complete search history.

(56) References Cited

U.S. PATENT DOCUMENTS 6,740,520 B1 * 5/2004 Goddard et al. ............ 435/325

FOREIGN PATENT DOCUMENTS

WO WO94/01548 * 1/1994

OTHER PUBLICATIONS

Phillimore, B. Locus HSJ503F13, Jul. 3, 1999. Accessed Mar. 1, 2005 (see attached computer printout).*

* cited by examiner

*Primary Examiner*—Lorraine Spector
*Assistant Examiner*—Dong Jiang
(74) *Attorney, Agent, or Firm*—Fulbright & Jaworski LLP

(57) ABSTRACT

The invention relates to soluble proteins which bind to the molecule known as IL-TIF/IL-22. The proteins can antagonize the effect of IL-TIF/IL-22 on target cells. The nucleic acid molecules encoding the proteins, and uses of the protein, are also described.

8 Claims, 7 Drawing Sheets

Figure 1A:
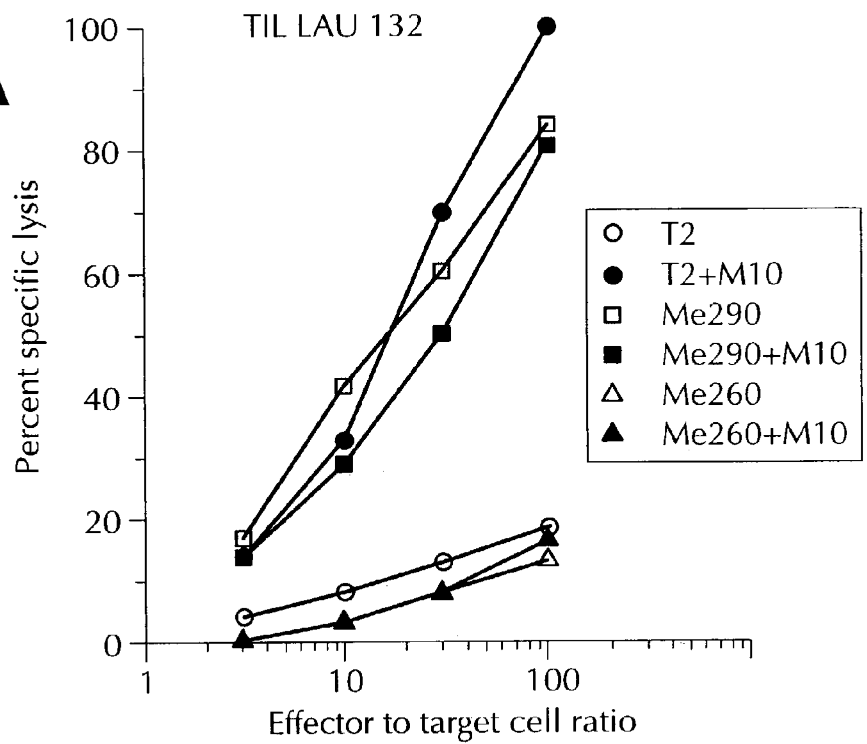
Figure 1B:
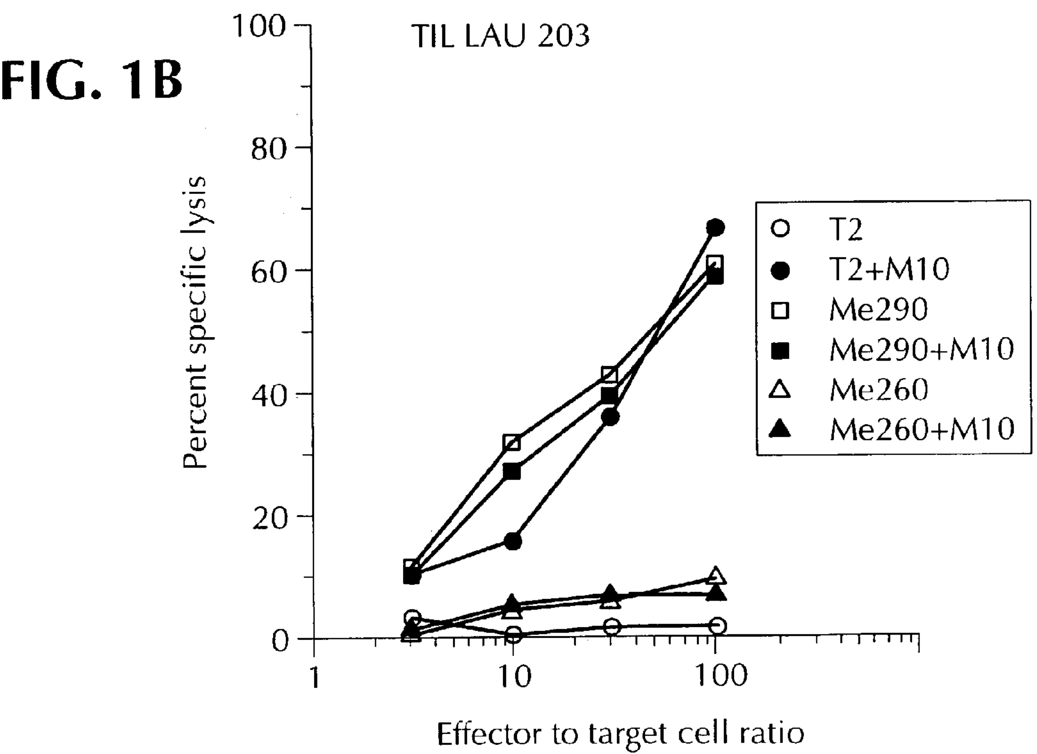
Figure 2A:
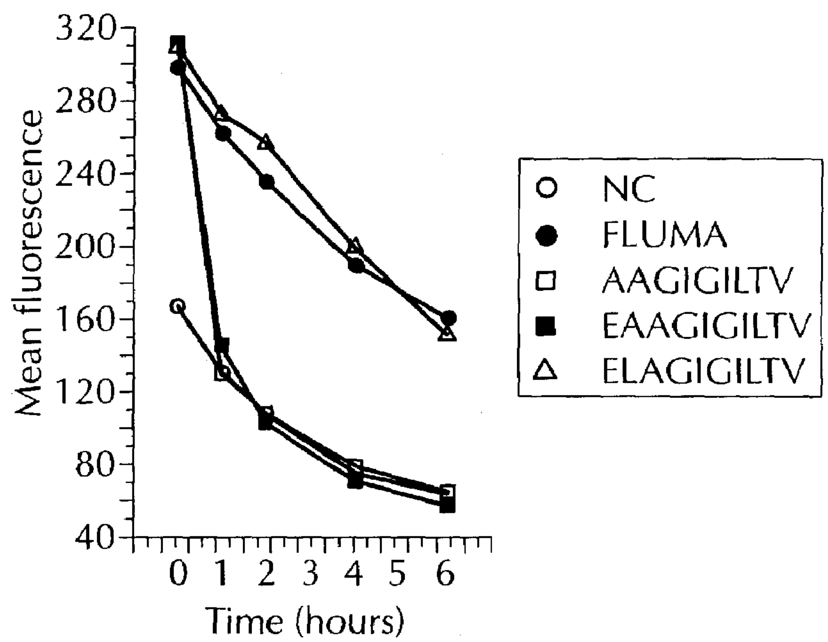
Figure 2B:
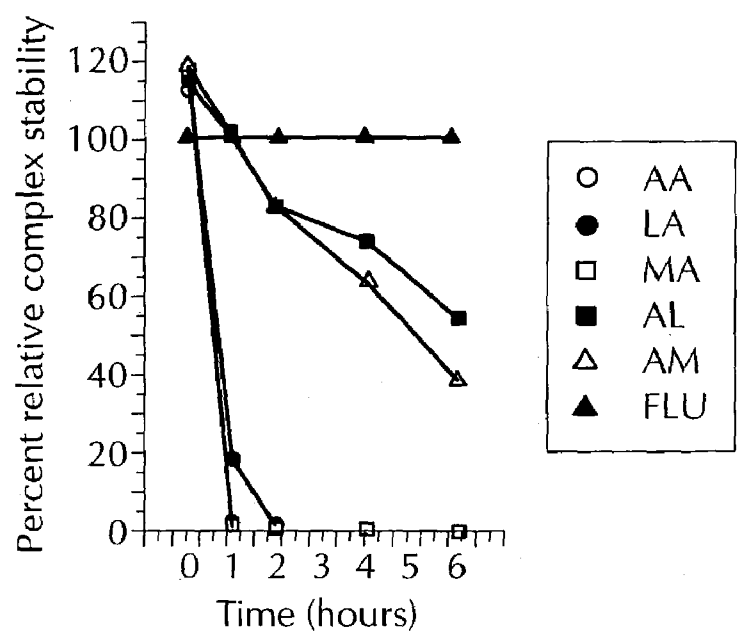
Figure 2C:
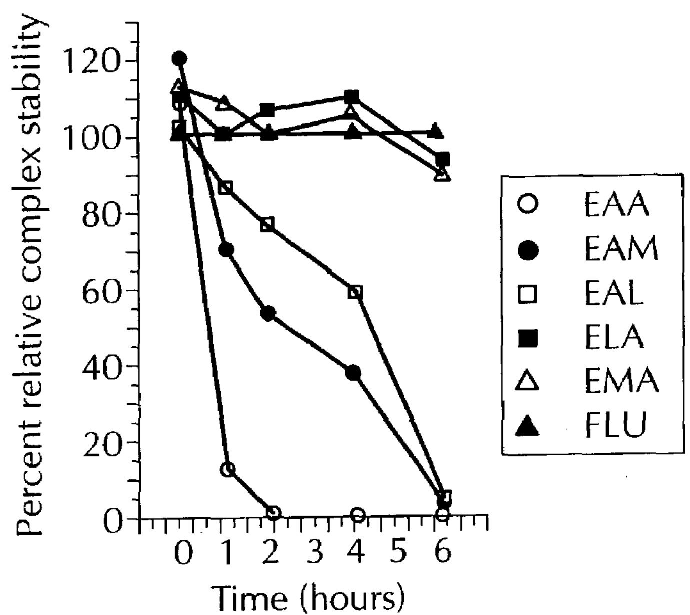
Figure 2D:
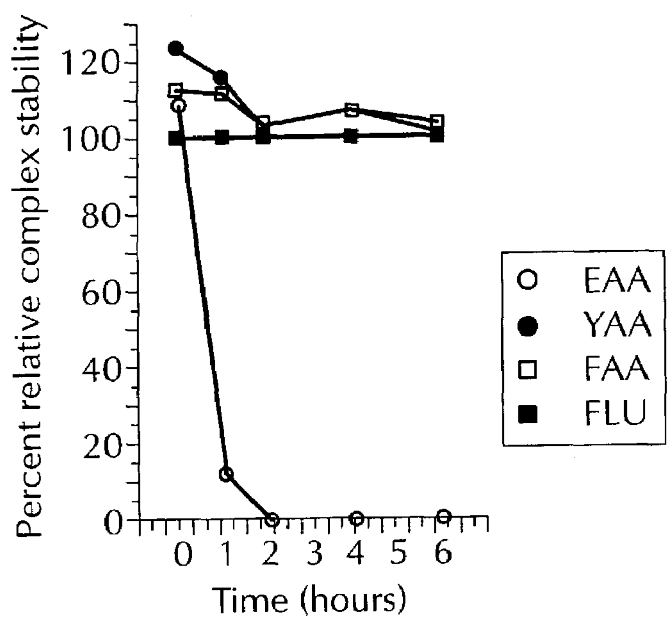
Figure 3A:
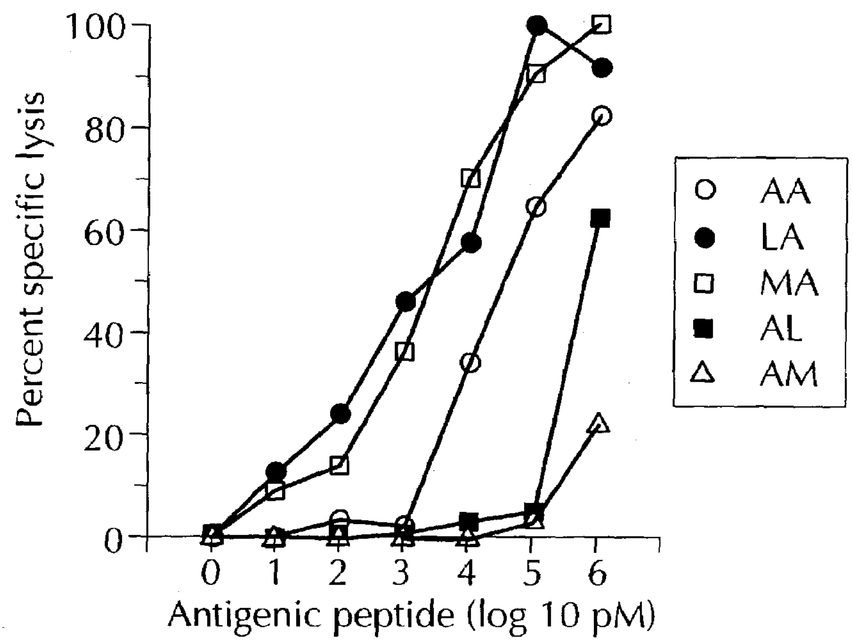
Figure 3B:
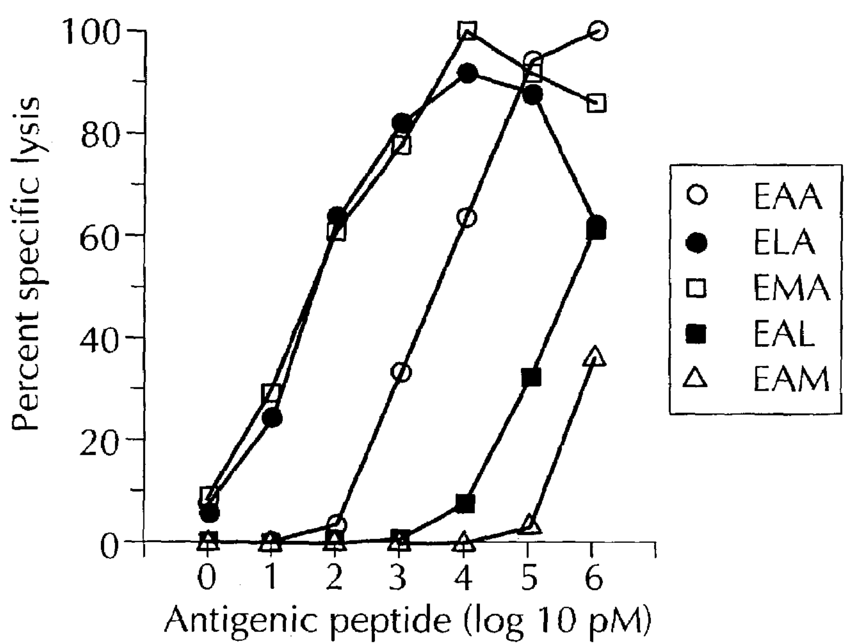
Figure 3C:
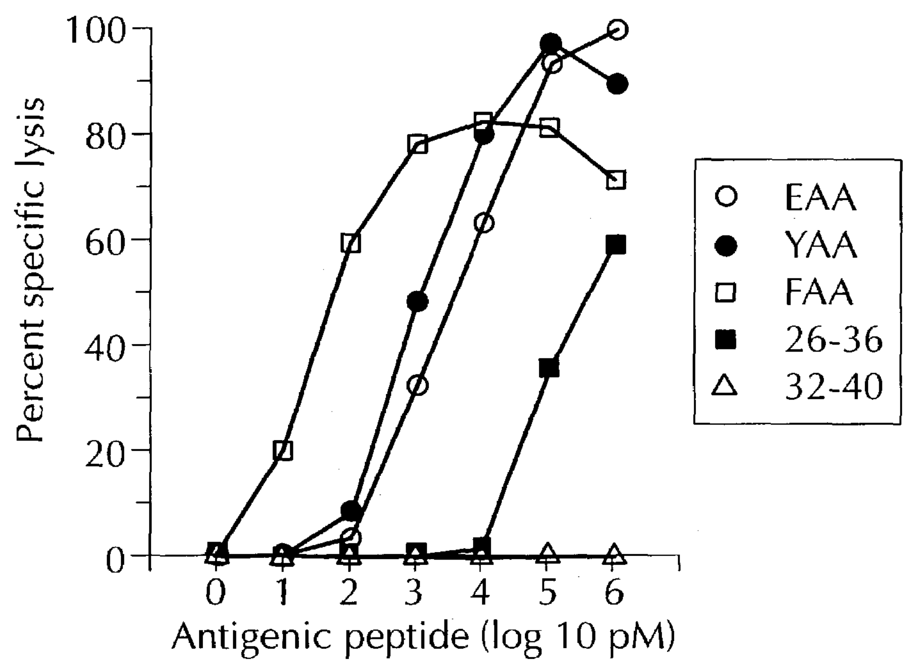
Figure 3D:
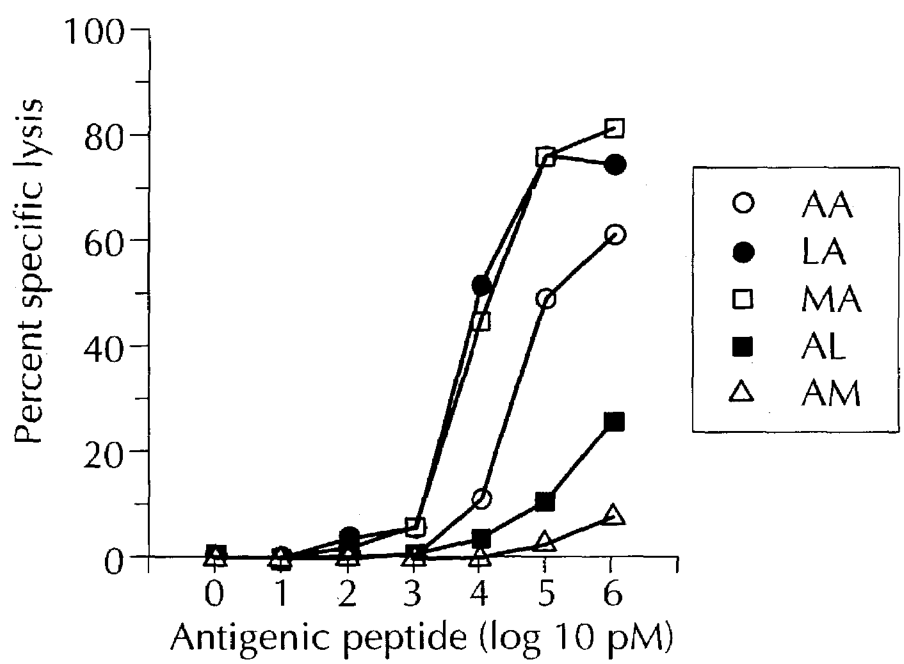
Figure 3E:
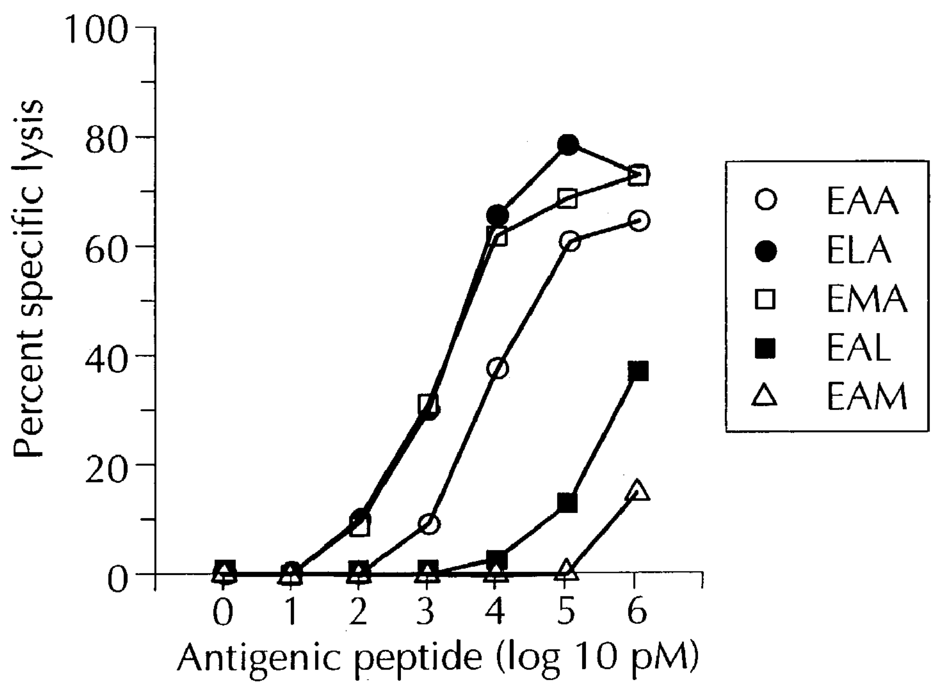
Figure 3F:
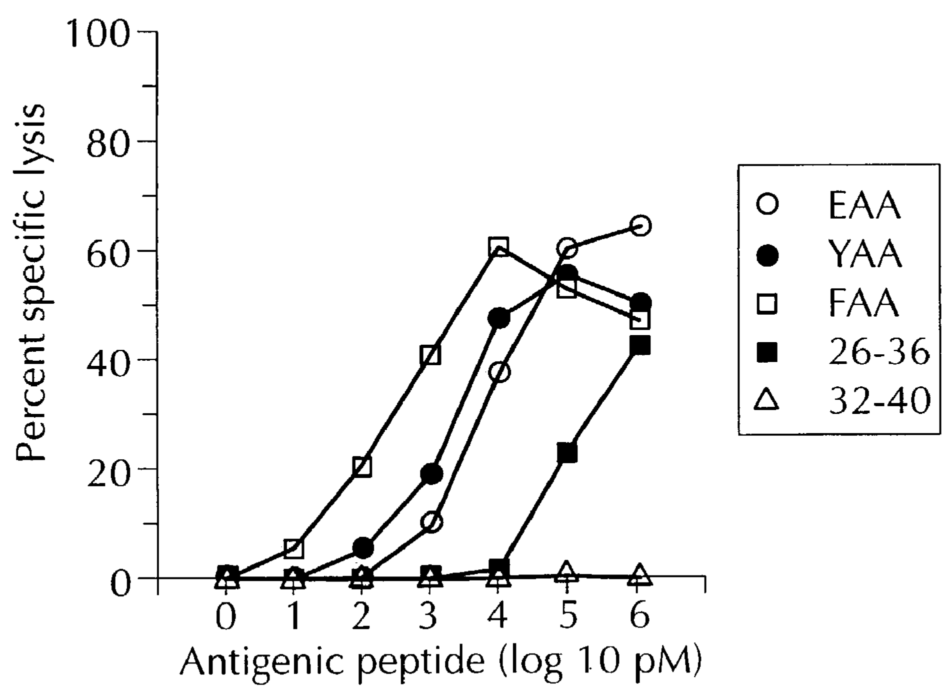
Figure 4A:
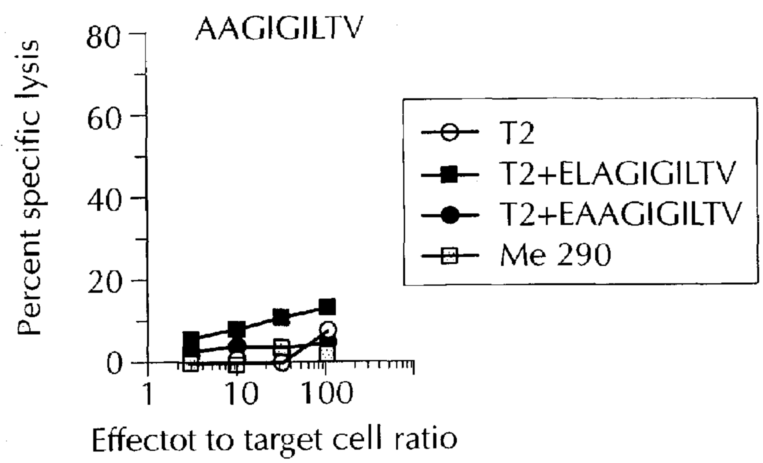
Figure 4B:
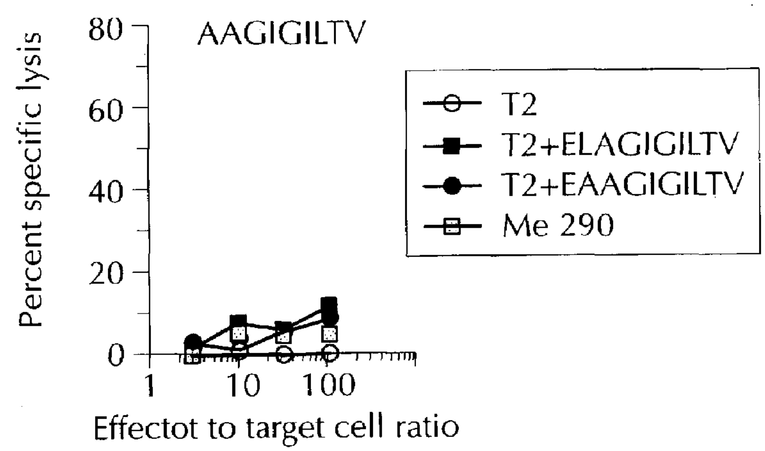
Figure 4C:
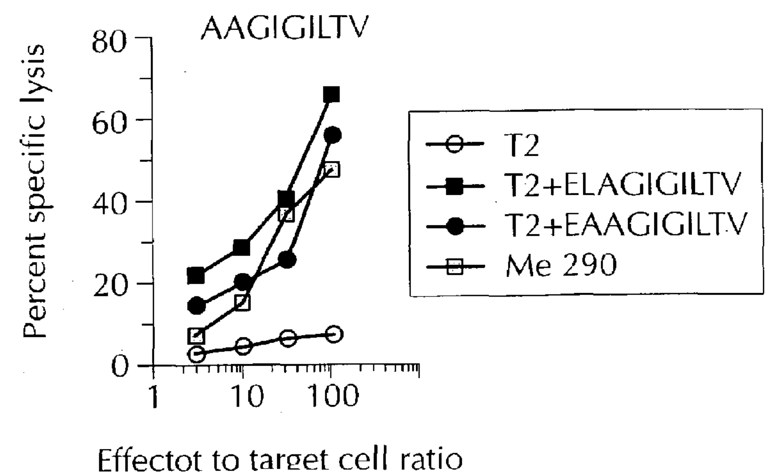

TIL LAU 132
Percent specific lysis
Effector to target cell ratio
T2
T2+M10
Me290
Me290+M10
Me260
Me260+M10
0
20
40
60
80
100
1
10
100

TIL LAU 203
Percent specific lysis
Effector to target cell ratio
T2
T2+M10
Me290
Me290+M10
Me260
Me260+M10
0
20
40
60
80
100
1
10
100

ISOLATED NUCLEIC ACID MOLECULES WHICH ENCODE A SOLUBLE IL-TIF/IL-22 RECEPTOR OR BINDING PROTEIN WHICH BINDS TO IL-TIF/IL-22, AND USES THEREOF

RELATED APPLICATIONS

This application is a national phase application of international application PCT/US01/29576, filed Sep. 21, 2001, and claims priority thereof. The international application, in turn, claims priority of Ser. No. 09/919,162, filed Jul. 30, 2001, and of provisional applications 60/245,495, filed Nov. 3, 2000, and 60/234,583, filed Sep. 22, 2000, all of which are incorporated by reference in their entirety.

FIELD OF THE INVENTION

This invention relates to newly isolated nucleic acid molecules, proteins and their uses. More specifically, it relates to a soluble protein which binds to the molecule referred to as IL-TIF/IL-22 or as it will be referred to hereafter "IL-22BP" or "IL-22 binding protein." The proteins of the invention inhibit TIF/IL-22 by binding thereto, and inhibiting IL-TIF/IL-22's effect on cells.

BACKGROUND AND PRIOR ART

The last decade has seen knowledge of the immune system and its regulation expand tremendously. One area of particular interest has been that of research on the proteins and glycoproteins which regulate the immune system. One of the best known families of these molecules are the cytokines. These are molecules which are involved in the "communication" of cells with each other. The individual members of the cytokine family have been found to be involved in a wide variety of pathological conditions, such as cancer and allergies. Whereas sometimes the cytokines are involved in the pathology of the condition, they are also known as being therapeutically useful.

Interleukins are one type of cytokine. The literature on interleukins is vast. An exemplary, but by no means exhaustive listing of the patents in this area includes U.S. Pat. No. 4,778,879 to Mertelsmann et al.; U.S. Pat. No. 4,490,289 to Stern; U.S. Pat. No. 4,518,584 to Mark et al.; and U.S. Pat. No. 4,851,512 to Miyaji et al., all of which involve interleukin-2 or "IL-2." Additional patents have issued which relate to interleukin-1 ("IL-1"), such as U.S. Pat. No. 4,808, 611 to Cosman. The disclosure of all of these patents are incorporated by reference herein. More recent patents on different interleukins include U.S. Pat. Nos. 5,694,234 (IL-13); 5,650,492 (IL-12); 5,700,664, 5,371,193 and 5,215,895 (IL-11); 5,728,377, 5,710,251, 5,328,989 (IL-10); 5,580, 753, 5,587,302, 5,157,112, 5,208,218 (IL-9); 5,194,375, 4,965,195 (IL-7); 5,723,120, 5,178,856 (IL-6), and 5,017, 691 (IL-4). Even a cursory review of this patent literature shows the diversity of the properties of the members of the interleukin family. One can assume that the larger cytokine family shows even more diversity. See, e.g., Aggarwal et al., ed., *Human Cytokines: Handbook For Basic And Clinical Research* (Blackwell Scientific Publications, 1992), Paul, ed., *Fundamental Immunology* (Raven Press, 1993), pg 763-836, *"T-Cell Derived Cytokines And Their Receptors"*, and "*Proinflammatory Cytokines and Immunity*," and Thomson, ed. "*The Cytokine Handbook*" (1998, Academic Press). All cited references are incorporated by reference.

The relationships between various cytokines are complex. As will be seen from the references cited herein, as the level of a particular cytokine increases or decreases, this can affect the levels of other molecules produced by a subject, either directly or indirectly. Among the affected molecules are other cytokines.

The lymphokine IL-9, previously referred to as "P40," is a T-cell derived molecule which was originally identified as a factor which sustained permanent antigen independent growth of T4 cell lines. See, e.g., Uyttenhove et al., *Proc. Natl. Acad. Sci*. 85: 6934 (1988), and Van Snick et al., *J. Exp. Med*. 169: 363 (1989), the disclosures of which are incorporated by reference, as is that of Simpson et al., *Eur. J. Biochem*. 183: 715 (1989).

The activity of IL-9 was at first observed on restricted T4 cell lines, failing to show activity on CTLs or freshly isolated T cells. See, e.g., Uyttenhove et al., supra, and Schmitt et al., *Eur. J. Immunol*. 19: 2167 (1989). This range of activity was expanded when experiments showed that IL-9 and the molecule referred to as T cell growth Factor III ("TCGF III") are identical to MEA (Mast Cell Growth Enhancing Activity), a factor which potentiates the proliferative response of bone marrow derived mast cells to IL-3, as is described by Hüiltner et al., *Eur. J. Immunol*. 19: 2167 (1989) and in U.S. Pat. No. 5,164,317, the disclosures of both being incorporated by reference herein. It was also found that the human form of IL-9 stimulates proliferation of megakaryoblastic leukemia. See Yang et al., *Blood* 74: 1880 (1989). Recent work on IL-9 has shown that it also supports erythroid colony formation (Donahue et al., *Blood* 75(12): 2271–2275 (6–1990)); promotes the proliferation of myeloid erythroid burst formation (Williams et al., Blood 76: 306–311 (1990)); and supports clonal maturation of BFU-E's of adult and fetal origin (Holbrook et al., *Blood* 77(10): 2129–2134 (1991)). Expression of IL-9 has also been implicated in Hodgkins's disease and large cell anaplastic lymphoma (Merz et al., *Blood* 78(8): 1311–1317 (1990)). Genetic analyses of mice that were susceptible or resistant to the development of bronchial hyperresponsiveness have unraveled a linkage with the IL-9 gene as well as a correlation between IL-9 production and susceptibility in this model (Nicolaides et al., *Proc. Natl. Acad. Sci. USA*, 94, 13175–13180, (1997)). Human genetic studies also point to the IL-9 and IL-9R or "IL-9 receptor" genes as candidates for asthma therapy (Doull et al., *Am. J. Respir. Crit. Care Med*., 153, 1280–1284, (1996); Holroyd et al., *Genomics* 52, 233–235, (1998)). IL-9 transgenic mice allowed for the demonstration that increased IL-9 expression results in lung mastocytosis, hypereosinophilia, bronchial hyperresponsiveness and high levels of IgE (Temann et al., *J. Exp. Med*. 188, 1307–1320 (1998); Godfraind et al., *J. Immnunol*. 160, 3989–3996 (1998); McLane et al., *Am. J. Resp. Cell. Mol*. 19:713–720 (1999)). Taken together, these observations strongly suggest that IL-9 plays a major role in this disease Additional work has implicated IL-9 and muteins of this cytokine in asthma and allergies. See, e.g. PCT Application US96/12757 (Levitt, et al.), and PCT US97/21992 (Levitt, et al.), both of which are incorporated by reference.

IL-9 is known to affect the levels of other molecules in subjects. See Louahed et al., *J. Immunol*. 154: 5061–5070 (1995), Demoulin et al., Mol. Cell. Biol. 16: 4710–4716 (1996), both incorporated by reference. It will be recognized that the molecules affected have their own functions in biological systems. For example, Demoulin et al. show that many of the known activities of IL-9 are mediated by activation of STAT transcription factors. As such, there is continued interest in trying to identify molecules whose presence and/or level is affected by other molecules, such as signal transduction molecules and cytokines.

A new member of the interleukin family is described in, e.g., U.S. patent application Ser. No. 09/419,568, filed Oct. 18, 1999, and incorporated by reference in its entirety. Also see Dumoutier, et al., "Human interleukin-10 related T cell derived inducible factor molecular cloning and function characterization as a hepatocyte stimulating factor," *Proc. Natl. Acad. Sci. USA* 97(18): 10144–10149 (2000), also incorporated by reference. Also see Dumoutier et al., *J. Immunol* 164:1814 (2000), and Dumoutier, et al., *Genes Immunol* 1:488 (2000), both of which are incorporated by reference. Also see Ser. No. 09/626, 627 filed Jul. 27, 2000, incorporated by reference. Dumoutier, et al., *Proc. Natl. Acad. Sci*. 97(18): 10144–10149 (2000) also suggest that this new molecule, IL-TIF/IL-22, induces acute phase reactant production by liver cells, in vitro, and in vivo. Xie, et al., *J. Biol. Chem* 27:31335–31339 (2000), have suggested that this molecule be renamed as IL-22. Xie et al also teach that the receptor for this molecule consists of two chains, each of which bind to the molecule. These chains are referred to as "CRF 2-4" and "CRF 2-9." The former is also referred to as "IL-10RB" because it is required for IL-10 signalling. See, e.g., Kotenko, et al., *EMBO J* 16:5894 (1997).

The second chain, CRF 2-9, was originally considered to be an orphan receptor. This chain is also known as "ZCYTOR 11," but Xie, et al., supra, have proposed it be renamed "IL-22R". Due to their structure, both chains are considered to belong to the class II cytokine receptor family (Kotenko et al., *Oncogene* 19:2557 (2000)), which consists of 8 members of known function (i.e., two pairs of two receptor subunits for type I interferons (IFN-α, IFN-β, IFN-w, IFN-t) and type II (IFN-γ) interferon, IL-10R, tissue factor, and the two chains referred to supra. At least one orphan receptor, referred to as "CRF 2-8," is also a member of the family. These receptors are related by their extracellular domains, which have tandem fibronectin type III (FNIII) domains. Four of the genes encoding these proteins, i.e., "IFNAR1," "IFNAR2," IIL10R2" and "IFNGR2," are located on human chromosome 21. The IFNGR1 and CRF2-8 genes map to chromosome 6, IL22R is located on chromosome 1, and IL10R1 is on chromosome 11.

Additional work on these molecules can be found in, e.g., International Patent Application Number PCT/US00/11479 (Publication Number WO 00/65027) and International Parent Application Number PCT/US99/11644 (Publication Number WO 99/61667). Also see International Patent Application Number PCT/US00/32703, publication number WO/01/40467, describing "ZCYTOR16."

A nucleic acid molecule has now been identified, which encodes another molecule which binds IL-TIF/IL-22 and is referred to as IL-22 binding protein (IL-22BP). The protein which the nucleic acid molecule encodes serves to inhibit the effect that IL-TIF/IL-22 has on target cells. Further, a second form of the nucleic acid molecule has been identified as a splice variant of the first. This second molecule contains an additional 96 nucleotides, and encodes an additional 32 amino acids.

These, as well as other features of the invention, will be seen in the disclosure which follows.

DETAILED DESCRIPTION OF PREFERRED EMBODIMENTS

EXAMPLE 1

This example describes experiments which were carried out to identify potential new members of the class II cytokine receptor family. Receptors for the interferons, and for IL-10, are members of this family.

The amino acid sequence of the extracellular domain of human IL-10R was used to screen the database of the Sanger Center using TBLASTN software.

Two short regions of homology were identified in a BAC clone from chromosome 6q24 (Genbank Accession Number AL 05337), about 40 kilobases from the known IFNGR-1 gene.

The first fragment showed 40% amino acid identity with residues 63–119 of IL-10R, while the other, located 3 kb upstream, showed 47% identity with residues 29–47.

Once the BAC sequence was identified, it was analyzed further, using the NIX analysis program. The software predicted a gene comprising 5 exons, stretching over about 16 kilobases, with the last exon corresponding to several EST sequences.

EXAMPLE 2

These experiments were designed to determine the pattern of tissue distribution of the molecule identified in example 1, supra.

Total RNA was isolated from samples taken from various organs using guanidium isothiocyanate lysis and CsCl gradient centrifugation, following Ausubel, et al., *Current Protocols In Molecular Biology* (1993), incorporated by reference. Samples of RNA (5 ug), were reverse transcribed with an oligo(dT) primer, and the resulting cDNA was amplified via PCR. Specifically, samples corresponding to 5 ng of total RNA were amplified using

```
agggtacaat ttcagtcccg a  (sense, SEQ ID NO: 1)
```

and

```
cggcgtcatg ctccattctg a. (antisense, SEQ ID NO: 2)
```

The annealing temperature was 55° C. Resulting PCR products were analyzed in ethidium bromide stained, 1% agarose gels.

Strongest expression was found in breast tissue, and a clear signal was also detected in lungs and the intestinal tract (i.e., stomach and colon). Skin, testis, brain, heart, and thymus tissue were also positive, at lower levels, and not in all samples tested. There was no detectable expression in prostate, bladder, kidney, ovary, muscle, bone marrow, liver or uterine tissue.

One noteworthy feature of these results was the identification of a second band in some tissue samples, such as skin and lungs. The significance of this second band is discussed infra.

EXAMPLE 3

These experiments describe work in amplifying full length cDNA for the materials described supra.

Breast tissue RNA was prepared, as described supra, and was amplified via RT-PCR, as described supra, using:

```
tgaacagtca cactcgagac  (sense; SEQ ID NO: 3)
catgatgc, and
catcctgttc tcgaggagct  (antisense; SEQ ID NO: 4)
ttaga.
```

These primers contain mutations which introduce an XhoI site to permit direct cloning into pCEP4 plasmid described infra. A cDNA molecule was identified which consisted of a 696 nucleotide open reading frame that encoded a protein of 230 or 231 amino acids, with a calculated molecular weight of about 27 kd. The complete nucleotide sequence included 2271 nucleotides, with the "ORF" at nucleotides 113–805, or 110–805. The nucleotide sequence, and the predicted amino acid sequence, are presented as SEQ ID NOS: 5 and 6. Note that there are two potential start codons adjacent to each other, so that the protein may begin with Met or Met Met.

Analysis of the predicted protein reveals a stretch of hydrophobic amino acids at the N-terminus, compatible with a signal peptide. There was significant homology to the extracellular domains of members of the IL-10 receptor family; however, the molecule under consideration lacked a hydrophobic transmembrane domain, suggesting it is a secreted protein.

When the deduced amino acid sequence was aligned with other proteins, 33% amino acid identity with the extracellular domain of IL-22R was found, as was 34% with orphan receptor CRF 2-8. Lower sequence identity was found with IL-10R (29%), CRF2-4/IL-10Rβ (30%), tissue factor (26%) and the four interferon receptor chains (23–25%). The predicted mature form of the protein contains 4 cysteine residues. These are conserved in most members of the class II cytokine receptors. Additionally, the structure of the gene, as deduced from the information presented herein, is of one that contains 5 exons, the first of which encodes the signal peptide, and the following four of which encode the mature protein.

EXAMPLE 4

The data developed supra showed that the molecule of interest had highest homology to the extracellular domain of IL-22R. Experiments were therefore designed to determine if the molecule bound to IL-TIF/IL-22.

A series of IL-22BP fusion proteins were made. The first, referred to as "IL-TIFR-Ig," was produced by first amplifying the full length open reading frame of the IL-22BP molecule referred to supra, using the following, mutated antisense primer:

```
ccaacttcca tgatcaatgg aatttccaca   (SEQ ID NO. 7)

catctct
```

This primer serves to introduce a BclI site into the stop codon of the ORF. In addition, a region comprising the hinge, CH2 and CH3 domains of murine IgG3 isotype heavy chain was amplified, using the known IgG3 anti-TNP hybridoma C3110. The following primers were used:

```
aagactgagt tgatcaagag  (sense, SEQ ID NO. 8)

aatcgagcct aga and

aatgtctaga tgctgttctc  (antisense, SEQ ID NO. 9)

atttacc
```

These primers also contain BclI and XbaI sites for cloning.

Following amplification, both PCR products were digested, and cloned into pCEP4 plasmid, under control of CMV promoter, as described supra.

Clones were sequenced, using standard methodologies. These were then used to transfect HEK293 cells transiently, also as described supra. In brief, cells were seeded in 6 well plates, at $3\times10^5$ cells/well, one day prior to transfection. Standard, lipofectamine methodologies were used, using 2 ug of plasmid DNA. After transfection, cells were incubated in 1.5 ml of normal medium for 3 days.

In similar fashion, a fusion protein of IL-22R and the IgG3 Fc fragment was generated, known as IL-22R-Ig. These two fusion proteins were used together with a control fusion protein, i.e. IL-9-Ig, which had been made previously.

Assays were then carried out by coating polystyrene plates with either 0.083 mg/ml of recombinant human IL-TIF/IL-22, or 0.2 mg/ul bovine serum albumin, in 20 mm Tris. Glycine buffer containing 30 mm NaCl, pH 9.2, overnight, at 4° C. Following washing in PBS buffer plus Tween 20 ($10^{-4}$) plates were blocked with PBS plus 1% BSA for two hours, and then 50 μl of supernatant from transiently transfected HEK293 cells was added. Plates were then incubated for 2 hours, at 37° C. Any bound fusion protein was detected, using murine anti-Ig polyclonal antibodies coupled to peroxidase. Detection was carried out using the peroxidase substrate "TMB", or (3,3',5, 5'-tetramethylbenzidine), and stopped by 20 μl $H_2S0_4$.

The results indicated that IL-22BP-Ig and IL-22R-Ig both bind to IL-TIF/IL-22, but not bovine serum albumin. Supernatants of mock transfected cells, or IL-9-Ig did not detectably bind IL-TIF/IL-22.

EXAMPLE 5

These experiments describe studies designed to assess whether the protein of the invention was able to block IL-TIF/IL-22 activity.

To test this, the cell lines H4IIE and HT-29, referred to supra, were used. It is known that H4IIE responds to IL-TIF/IL-22 by activation of STAT transcription factors, and acute phase reactant production. The HT-29 cell line shows STAT-3 activation. STAT activation by IL-TIF/IL-22 can be measured, in both cell lines, via the use of a luciferase reporter construct which includes 5 STAT binding sites, plus a minimal TK promoter. See Dumoutier, et al.; *Proc. Natl. Acad. Sci. USA*, 97:10144 (2000), incorporated by reference.

The construct "pGRR5" was used. This construct contains 5 copies of the STAT binding site of the FcγR1 gene, upstream of a luciferase gene under control of a tk promoter. As an internal control, the vector pRL-TK was used. This construct contains the renilla luciferase gene under the control of the tk promoter.

The H4IIE and HT-29 cells were electroporated with 15 μg of pGRR5 and 1 μg pRL-TK (250V, 192Ω, 1,200 μF), and were then seeded at $4\times10^5$ cells/well. RAW 264.7 cells were transfected in the same way, the only difference being the resistance used (74Ω). This cell line was used to determine the effect of the IL-22BP material on IL-10.

The transfected H4IIE or HT-29 cells were then stimulated with a preincubated (1 hour) mixture of recombinantly produced IL-TIF/IL-22, at varying concentrations and 5% supernatant (from HEK293 cells that had been transfected with the CDNA described herein), or a preincubated mixture of the IL-TIF and 5% supernatant from mock transfected cells. After two hours, luciferase activity was measured either in pelleted or lysed cells, or directly in plated cells, using a commercially available assay.

The results indicated that the STAT-activating activity of IL-TIF/IL-22 (at 4 ng/ml), was blocked completely when combined with supernatants from cells transfected by constructs encoding the IL-22BP protein or fusion proteins, described supra. This was the case for both H4IIE and HT-29 cells. In contrast, when IL-6 was used in place of IL-TIF/IL-22, there was no effect. Nor was IL-10 activity affected by pre-incubation with IL-IL-22BP protein or fusion protein.

EXAMPLE 6

Novick, et al, Cytokine 4:6 (1992), have shown that soluble IL-6 receptor can increase the sensitivity of cells to subliminal concentrations of its ligand. Studies were therefore carried out, in parallel to those presented supra, testing low (<25 ng/ml), and high (50–200 ng/ml) concentrations of IL-TIF/IL-22 in H4IIE cells. It was found that, at the low concentrations, STAT activation was blocked completely by IL-22BP but IL-22BP failed to block STAT activation in H4IIE cells, when high concentrations of IL-TIF were used. Decreasing the concentration of IL-22BP led to a loss of inhibitory effect, but did not reveal any potentiating activity for IL-TIF/IL-22.

EXAMPLE 7

Fernandez-Botran, et al., *J. Exp. Med* 174:673 (1991) have shown that the soluble and transmembrane forms of the IL-4 receptor have similar association rates, but the soluble form has a higher dissociation rate. This indicates that the complexes formed by IL-4 and the IL-4 binding protein ("IL-4BP") must be transient and reversible allowing the ligand to dissociate from one soluble receptor and become available for binding to another soluble receptor or to a membrane receptor from which it would dissociate more slowly. Experiments were carried out to determine if the protein of the invention exhibited the same property and thus delay rather than inhibit IL-TIF/IL-22 action.

It was found that the effect of IL-TIF/IL-22 on STAT-activation in HT-29 cells reached its peak after 4–6 hours, and decreased dramatically at 24 hours but the receptor of the invention had the same inhibitory effect throughout the assay, indicating that it could not delay IL-TIF/IL-22 activity in vitro.

EXAMPLE 8

Example 2, supra, referred to the identification of a second band in some tissue samples. The band was excised, and sequenced using an automated, fluorescence based system, and art recognized methods. The sequence, set forth at SEQ ID NO. 10, includes an additional 96 nucleotides, resulting in 32 additional amino acids in the predicted protein (SEQ ID NO. 11). The ORF for SEQ ID NO: 10 extends from nucleotide 109 or 112 to nucleotide 900. As with SEQ ID NOS: 10 & 11, there are two possible start codons.

The preceding examples disclose the aspects of this invention, including isolated nucleic acid molecules which encode a soluble, receptor-like antagonist of IL-TIF/IL-22 such as those with the amino acid sequence of the protein encoded by the nucleotide sequences set forth in SEQ ID NO: 5 or 10. It will be appreciated by one of ordinary skill that the degeneracy of the genetic code facilitates the preparation of nucleic acid molecules which may not be identical to the nucleotide sequence of SEQ ID NO: 5 or 10, but which encode the same protein. Of course, SEQ ID NO: 5 or 10 are preferred embodiments of this invention, but other embodiments are also a part of the invention. Genomic DNA, complementary DNA, and RNA, such as messenger RNA, are all to be included therein. Isolated nucleic acid molecules from other animal species, including other mammals, are also a part of the invention. A preferred aspect of the invention are isolated nucleic acid molecules whose complements hybridize to SEQ ID NO: 5 or 10 under stringent conditions. "Stringent conditions," as used herein, refer, for example, to hybridization at 65° C. in buffer (3.5×SSC), 0.02% Ficoll, 0.02% polyvinylpyrrolidone, 0.02% bovine serum albumin, 25 mM $NaH_2PO_4$ (pH 7), 0.1% SDS, 2 mM EDTA, followed by a final wash at 2×SSC, room temperature and then 0.1×SSC/0.2×SDS at temperatures as high as, e.g., about 65° C. More stringent conditions, such as 0.1×SSC, can also be used. These nucleic acid molecules encode proteins, such as those with amino acid sequences set forth at SEQ ID NO: 6 or 11. The soluble, receptor-like antagonist of this invention may be found in glycosylated or non-glycosylated, sulfated and non-sulfated forms and so forth. Also a part of the invention are isolated nucleic acid molecules which encode proteins having 30% or more, preferably 45% or more, more preferably 50% or more, 60% or more, 70% or more, 80% or more, or 90% or more, and most preferably 95% or more amino acid identity with an amino acid sequence of a protein encoded by SEQ ID NO: 5 or 10.

Amino acid sequence identity may be determined using the algorithm GAP (Genetics Computer Group, Madison, Wis.) or identity. GAP uses the Needleman and Wunsch algorithm to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST (which uses the method of Altschul et al. (1990) *J. Mol. Biol*. 215: 405–410), FASTA (which uses the method of Pearson and Lipman (1988) *PNAS USA* 85: 2444–2448), or the Smith-Waterman algorithm (Smith and Waterman (1981) *J. Mol Biol*. 147: 195–197), generally employing default parameters.

Also a part of the invention are expression vectors which include the nucleic acid molecules of the invention, operably linked to a promoter, so as to facilitate expression of the DNA. It is well within the skill of the artisan to prepare such vectors.

The vectors, as well as the nucleic acid molecules per se, can be used to prepare recombinant cells, such as isolated recombinant cells, be these eukaryotic or prokaryotic, wherein either an expression vector or the nucleic acid molecule itself is incorporated therein. *E. coli* cells, COS cells, CHO cells, Sf9 cells etc., are all examples of types of cells which may be used in accordance with this aspect of the invention.

Generally, nucleic acid molecules employed to produce a polypeptide or fragment thereof according to the present invention are provided as isolates, in isolated and/or purified form, or free or substantially free of material with which they are naturally associated, such as free or substantially free of nucleic acid molecules flanking the gene in the human genome, except possibly one or more regulatory sequence(s) for expression. Nucleic acid molecules may be wholly or partially synthetic and may include genomic DNA, cDNA or RNA.

Nucleic acid molecules encoding the peptides or polypeptides of the present invention may be readily prepared by the skilled person using the information and references contained herein and techniques known in the art (for example, see Sambrook and Russell "Molecular Cloning, A Laboratory Manual", Third Edition, Cold Spring Harbor Laboratory Press, 2001, and Ausubel et al, Current Protocols in Molecular Biology, John Wiley and Sons, 1992, or later edition thereof).

In order to obtain expression of a nucleic acid molecule of the invention, this may be incorporated in a vector having one or more control sequences operably linked to the nucleic acid molecule to control its expression. Vectors may be chosen or constructed. They may contain appropriate regulatory sequences, including promoter sequences, terminator fragments, polyadenylation sequences, enhancer sequences, marker genes and other sequences as appropriate, e.g. nucleotide sequences so that the polypeptide or peptide is produced as a fusion and/or nucleic acid encoding secretion signals so that the polypeptide or peptide produced in the host cell is secreted from the cell. Vectors may be plasmids, viral e.g. phage, or phagemid, as appropriate. Encoded product may then be obtained by transforming the vectors into host cells in which the vector is functional, culturing the host cells so that the product is produced and recovering the product from the host cells or the surrounding medium.

A further aspect provides a method which includes introducing a nucleic acid molecule of the invention into a host cell. The introduction, which may (particularly for in vitro introduction) be generally referred to without limitation as "transformation" or "transfection", may employ any available technique. For eukaryotic cells, suitable techniques may include calcium phosphate transfection., DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed. Marker genes such as antibiotic resistance or sensitivity genes may be used in identifying clones containing nucleic acid of interest, as is well known in the art.

The introduction may be followed by causing or allowing expression from the nucleic acid molecule, e.g. by culturing host cells (which may include cells actually transformed although more likely the cells will be descendants of the transformed cells) under conditions for expression of the gene, so that the encoded product is produced. If the product as expressed is coupled to an appropriate signal leader peptide, it may be secreted from the cell into the culture medium. Following production by expression, a product may be isolated and/or purified from the host cell and/or culture medium, as the case may be, and subsequently used as desired, e.g. in an assay or test as disclosed herein.

Note also that expression may also be carried out in in vitro systems, e.g. reticulocyte lysate.

Following production of a polypeptide or peptide as identified herein, it may be tested for ability to bind IL-TIF/IL-22 and/or for ability to modulate binding of IL-22BP to IL-TIF/IL-22.

A further aspect of the present invention provides a host cell containing a heterologous nucleic acid molecule encoding a polypeptide or peptide as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

Proteins encoded by the above referenced nucleic acid molecules, preferably in isolated form, are another feature of this invention. By "protein" is meant both the immediate product of expression of the nucleic acid molecules, glycosylated forms of it, forms of the molecule following peptide signal cleavage, such as mature and/or processed forms of the protein, as well as multimeric forms, such as dimers, trimers, and so forth. Also a part of the invention are multimers, such as dimers, which contain at least one protein molecule of the invention, and at least one, different protein molecule. These multimers may be homomeric or heteromeric, such as heteromeric forms that include at least one molecule of a different soluble receptor, a transmembrane receptor, and so forth. Such multimers may bind only a single specific ligand. Also a part of the invention are complexes of the IL-22BP and a ligand, which then act as heteromeric cytokines in transmembrane receptors. Such structures parallel, e.g., the structure of IL-12. Also a feature of this invention is a protein consisting of the sequence set forth in SEQ ID NO: 6 or 11. Also included as a feature of this invention are proteins that are essentially identical to the sequence in SEQ ID NO: 6 or 11 having only conservative amino acid substitutions. Also included as a feature of the inventions are constructs, such as fusion proteins, where all or a part of the proteins described supra are linked in some fashion, e.g., to a "fusion partner" at least one additional protein or peptide, or amino acid sequence. The "fusion partner" may be, for example, a molecule which provides a recognizable signal, either directly or indirectly, such as a FLAG peptide, β-galactosidase, luciferase, an Fc immunoglobulin, a fluorescent protein, such as "GFP" (green fluorescent protein), and so forth. Other labels, such as radiolabels, particles, other enzymes, metals such as gold sols, may also be used. These fusion partners are preferably joined to the molecule which is described supra at the N- and/or C-terminus of the protein; however, it is to be understood that there are many techniques known for joining molecules to amino acids, and any and all of these methodologies can produce constructs which are a part of the invention.

The individual protein molecules of the invention will preferably have a molecular weight of from about 23 to about 40 kilodaltons as determined by SDS-PAGE. In multimeric forms, the molecular weight of the complex will, of course, vary, but the individual molecules contained therein will each have a molecular weight of about 23–40 kilodaltons, as determined by SDS-PAGE. These molecular weights, it is to be understood, refer to monomeric proteins. Glycosylated monomers will have higher molecular weights, e.g., up to at least about 40–50 kilodaltons.

The proteins preferably consist of at least about 180 and no more than about 300 amino acids. More preferably, the protein consists of about 230–275, more preferably 230–268, most preferably 231–263 amino acids. Preferably, the amino acids sequences consists of or comprises all or part of the amino acid sequences encoded by SEQ ID NO: 6 or 11. Such binding proteins can be produced via, e.g., transforming host cells with one or more nucleic acid molecules or expression vectors in accordance with the invention, culturing the transformant, and then isolating the resulting, recombinant binding protein.

It will be appreciated by the skilled artisan that the proteins and peptides encoded by the above recited nucleic acid molecules are a feature of the invention, and may be used to produce antibodies, in accordance with standard protocols. Such antibodies, in monoclonal and polyclonal form, constitute a further feature of the invention as do fragments of said antibodies, chimeric forms, humanized forms, recombinant forms, hybridoma cell lines which produce the antibodies and so forth.

Antibody molecules directed to IL-22BP, especially a region involved in binding to IL-TIF/IL-22, are also provided by a further aspect of the present invention. Such antibody molecules are useful for inhibiting IL-22BP binding to IL-TIF/IL-22, also for purifying IL-22BP.

Antibody molecules may be obtained using techniques which are standard in the art. Methods of producing antibodies include immunising a mammal (e.g. mouse, rat, rabbit, horse, goat, sheep or monkey) with the relevant polypeptide or a peptide fragment thereof. Antibody molecules may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunizing a mammal with a peptide or polypeptide, an antibody molecule may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibody molecules useful in accordance with the present invention may be modified in a number of ways. Indeed the term "antibody molecule" should be construed as covering antibody fragments and derivatives able to bind antigen. Examples of antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Hybridomas capable of producing antibodies with desired binding characteristics are within the scope of the present invention, as are host cells, eukaryotic or prokaryotic, containing nucleic acid molecules encoding antibodies (including antibody fragments) and capable of their expression. The invention also provides methods of production of the antibody molecules including growing a cell capable of producing the antibody under conditions in which the antibody is produced, and preferably secreted. Such methods generally comprise isolation or purification of antibody molecules from the cells or culture medium.

The reactivities of antibody molecules on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibody molecules may also be used in purifying and/or isolating a polypeptide chain of the invention, or a peptide fragment, for instance following production of a polypeptide by expression from encoding nucleic acid. Antibody molecules may be useful in a therapeutic context (which may include prophylaxis) to disrupt binding of polypeptides or other molecules with a view to inhibiting the relevant biological function or activity.

Also a feature of the invention are immunogens, comprising all or a part of the amino acid sequence of protein molecules of the invention, preferably combined with an adjuvant, such as Complete or Incomplete Freund's Adjuvant. An immunogenic or antigenic fragment of IL-22BP useful for obtaining antibody molecules may comprise or consist of one or more epitopes of IL-22BP. Linear epitopes are generally 5–8 amino acids in length, and peptides consisting of or comprising one or more epitopes or antigenic determinants of IL-22BP are provided as a further aspect of the invention. Portions of the protein sequences may be linked to other molecules, such as keyhole limpet hemocyanin, to render them more immunogenic.

A "fragment" of a polypeptide generally means a stretch of amino acid residues of at least about five contiguous amino acids, often at least about seven contiguous amino acids, typically at least about nine contiguous amino acids, more preferably at least about 13 contiguous amino acids, and, more preferably, at least about 20 to 30 or more contiguous amino acids. A peptide fragment may be 5, 6, 7, 8, 9 or 10, 5 to 10, 5 to 20, 10 to 20, 10–30, 20–30, 20–40, 30–40 or less than 40 amino acids in length.

As noted, peptides may be made recombinantly by expression from encoding nucleic acid. Peptides can also be generated wholly or partly by chemical synthesis. They can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

A further aspect of the present invention provides a method of obtaining an antibody directed against and preferably specific for IL-22BP, the method comprising bringing a population or panel of antibody molecules of diverse binding specificity into contact with an IL-22BP polypeptide or an antigenic or immunogenic fragment thereof, and selecting one or more antibody molecules that binds the polypeptide or fragment thereof. Preferably an antibody molecule that binds the polypeptide or fragment thereof is tested for specificity of its binding for the polypeptide or fragment thereof, e.g. by testing binding on a panel of unrelated antigens, for example by ELISA as is standard in the art. Preferably an antibody molecule specific for IL-22BP is identified.

A population of antibody molecules may for example be provided as a phage display library and brought into contact with the polypeptide or fragment thereof in vitro. Another of the various options available to the skilled person is to administer a peptide or polypeptide to a mammal in order to raise an immune response. Antibody molecules and/or cells producing antibody molecules can be taken or harvested from the animal or its serum, and tested for the desired property or properties.

Once obtained, an antibody molecule can be formulated into a composition comprising at least one additional component, such as a pharmaceutically acceptable excipient or carrier, and may be used as desired.

As noted, antibody molecules can be used, e.g., to determine if the proteins of the invention are present. This is a further feature of the invention, as is explained elsewhere herein.

It has been shown, in the examples, that the nucleic acid molecules of the invention encode proteins that block IL-TIF/IL-22 activity. Hence, a further feature of the invention is a method inhibiting IL-TIF/IL-22 activity, such as the activation of STAT transcription factors and acute phase reactant production by contacting a sample with an amount of the protein of this invention sufficient to inhibit or block the activity of IL-TIF/IL-22.

One could also use these molecules to test the efficacy of IL-9 agonists or antagonists when administered to a subject, such as a subject suffering from lymphoma, an immune system disorder such as an allergy, acquired immune deficiency syndrome, autoimmune diabetes, thyroiditis, or any of the other conditions described in, e.g, U.S. Pat. No. 5,830,454; 5,824,551, and pending application Ser. No. 08/925,348, filed on Sep. 8, 1997 now allowed, all of which are incorporated by reference. The molecules can also be used to modulate the role of IL-9 in these and other conditions. To elaborate, since IL-9 induces IL-TIF/IL-22 and the proteins of this invention block the activity of IL-TIF/IL-22, the proteins of this invention are useful as IL-9 activity modulators. Thus, a further aspect of the invention is a method to determine activity of endogenous IL-9, such as in situations where excess IL-9 activity is implicated, including asthma, allergies, and lymphomas. One can also block or inhibit IL-9 activity by blocking or inhibiting IL-TIF/IL-22 or IL-TIF/IL-22 activity, using the receptor-like antagonist of this invention. Examples of conditions which can be treated by the use of the protein or peptide of this invention are allergies, asthma, lymphoma, and so forth. The ability to regulate IL-9 activity is important in conditions such as those listed supra, as well as conditions such as apoptosis, including cortisol induced apoptosis, conditions involving the nuclear expression of BCL-3, since IL-9 is known to induce such expression, and so forth.

IL-TIF/IL-22 type molecules may either promote regeneration or inhibit differentiation of tissue types in which these molecules are active. IL-TIF/IL-22 molecules target various cancer and normal cell lines (i.e., mesangial and neuronal cells, as well as melanoma and hepatoma cells. See, e.g., U.S. patent application 09/626,617 filed Jul. 27, 2000, incorporated by reference). Hence, another feature of the invention is a method of treatment of a patient in need thereof wherein the proteins of this invention are used to inhibit the activity of IL-TIF/IL-22, in, e.g., neoplastic tissue, such as melanoma or hepatoma.

It will be clear to the skilled artisan that IL-TIF/IL-22 can regulate the inflammatory response. A preferred aspect of this regulation is the modulation of the acute phase response by organs, such as the liver, by administering the receptor-like antagonist of this invention. See, e.g., Janeway et al., *Immunobiology*, (4$^{th}$ edition), incorporated by reference. Janeway explains that various cytokines such as IL-1, IL-6 and TNF-α activate hepatocytes to synthesize acute phase proteins, such as c-reactive protein, and mannan binding lectin, as well as those described in the examples, supra.

IL-TIF/IL-22 has a role in activating acute phase proteins. Thus another aspect of this invention is a method for reducing the production of acute phase proteins, stimulated by IL-TIF/IL-22, by administering an amount of the receptor-like antagonist of this invention to a tissue sample or to a patient in need thereof, wherein said amount is sufficient to reduce production or activity of acute phase proteins.

Also a part of the invention are methods for regulating activity of IL-TIF/IL-22 by administering the receptor-like antagonist to regulate IL-TIF/IL-22 activity.

As noted, IL-22BP fragments that inhibit binding of the ligand to the receptor may be used, as may antibody molecules, and small molecules or other agents identified using for example an assay of the invention as disclosed herein. Accordingly, disclosure of aspects of the invention making use of IL-22BP in therapeutic, prophylactic or diagnostic contexts should be taken as disclosure of analogous aspects of the invention making use of any one or more of an IL-22BP fragment or fragments, an antibody molecule that binds and preferably is specific for IL-22BP, especially an antibody molecule that affects binding of IL-22BP to IL-TIF/IL-22, and an agent identified using an assay of the invention, able to modulate IL-22BP binding to IL-TIF/IL-22.

Whether a protein, polypeptide, peptide, antibody molecule, small molecule or other substance is to be employed for a therapeutic purpose, e.g. in treatment of a condition identified herein, in various further aspects, the present invention further provides a pharmaceutical composition, medicament, drug or other composition for such a purpose, the composition comprising one or more such substances, the use of such a substance in a method of medical treatment, a method comprising administration of such a substance to a patient, e.g. for treatment (which may include preventative treatment) of a medical condition, use of such a substance in the manufacture of a composition, medicament or drug for administration for such a purpose, e.g. for treatment of a medical condition, and a method of making a pharmaceutical composition comprising admixing such a substance with a pharmaceutically acceptable excipient, vehicle or carrier, and optionally other ingredients.

Whatever the substance used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Examples of techniques and protocols mentioned above can be found in Remington's Pharmaceutical Sciences, 16th edition, Osol, A. (ed), 1980.

Instead of administering such substances directly, they may be produced in target cells by expression from an encoding nucleic acid introduced into the cells, e.g. from a viral vector or as "naked" DNA administered to the body. Nucleic acid encoding the substance e.g. a peptide able to modulate, e.g. interfere with, the interaction of IL-22BP and IL-TIF/IL-22, may thus be used in methods of gene therapy, for instance in treatment of individuals, e.g. with the aim of preventing or curing (wholly or partially) a disorder.

A polypeptide or peptide of the invention can be used in assaying for agents and substances that, by affecting the association or interaction between IL-TIF/IL-22 and IL-22BP, modulate IL-TIF/IL-22 function in vivo. Formats that may be used in such assays are described in detail below, and may comprise determining binding between components in the presence or absence of a test substance and/or determining ability of a test substance to modulate a biological or cellular function or activity in which binding of IL-22BP to IL-TIF/IL-22 plays a role. Assay methods that involve determination of binding between components and the effect of a test substance on such binding need not necessarily utilize full-length wild-type polypeptide chains. For instance, fragments of IL-22BP that retain ability to bind IL-22 may be employed, and vice versa. Indeed, as discussed further below, fragments of the polypeptides themselves represent a category of putative inhibitors, that may be used to interfere with binding between polypeptides.

Assays employing polypeptides and fragments thereof according to the invention may take any of a variety of formats.

One further aspect of the present invention provides an assay method for a substance able to interact with the relevant region of IL-22BP that binds to IL-TIF/IL-22, or the relevant region of IL-TIF/IL-22 that binds IL-22BP, as the case may be, the method comprising:

(a) bringing into contact an IL-22BP polypeptide or fragment thereof that binds IL-TIF/IL-22; or an IL-TIF/IL-22 polypeptide or a fragment thereof that binds IL-22BP, and a test compound; and (b) determining interaction or binding between said polypeptide or fragment thereof and the test compound.

A test compound found to interact with or bind to the relevant portion of the polypeptide may be tested for ability to modulate, e.g. disrupt or interfere with, binding between IL-TIF/IL-22 and IL-22BP, or to modulate an activity mediated by IL-TIF/IL-22.

In a further aspect the present invention provides an assay method for an agent that modulates binding of a IL-TIF/IL-22 to IL-22BP, the method comprising:

contacting an IL-TIF/IL-22 polypeptide or fragment with an IL-22BP polypeptide or fragment thereof and a test substance, under conditions in which in the absence of the test substance being an inhibitor of binding of IL-22BP to IL-TIF/IL-22 the IL-22BP polypeptide or fragment thereof binds the IL-TIF/IL-22 polypeptide or fragment thereof, and determining binding of the IL22-BP polypeptide or fragment thereof to the IL-TIF/IL-22 polypeptide or fragment thereof.

Modulation of binding identifies the test substance as an agent that modulates binding of IL-22BP to IL-TIF/IL-22.

In a further aspect according to the present invention there is provided an assay method for an agent that modulates biological activity of IL-22BP of the invention, the method comprising providing an IL-22BP polypeptide under test conditions, and determining IL-22BP activity in the presence and absence of a test substance.

In different assays of the invention, interaction and/or binding and/or activity of components in the presence of a test compound or substance may be compared with the interaction and/or binding and/or activity in comparable reaction medium and conditions in the absence of a test compound. A test compound able to modulate the interaction and/or activity may be identified. The skilled person is well aware of appropriate experimental controls to perform when conducting assay methods.

Compounds which may be screened may be natural or synthetic chemical compounds used in drug screening programmes. Extracts of plants, microbes or other organisms, which contain several characterised or uncharacterised components may also be used.

Also, combinatorial library technology provides an efficient way of testing a potentially vast number of different substances for ability to modulate an interaction. Such libraries and their use are known in the art, for all manner of natural products, small molecules and peptides, among others.

The use of peptide libraries may be preferred in certain circumstances. The potential for binding between polypeptide chains of receptors of the invention to be inhibited by means of peptide fragments of the polypeptide chains has been mentioned already. Such peptide fragments may consist of for example 10–40 amino acids, e.g. about 10, about 20, about 30 or about 40 amino acids, or about 10–20, 20–30 or 30–40 amino acids. These may be synthesized recombinantly, chemically or synthetically using available techniques.

In any assay method according to the invention, the amount of test substance or compound which may be added to an assay of the invention will normally be determined by trial and error depending upon the type of compound used. Even a molecule which has a weak effect may be a useful lead compound for further investigation and development.

A screening or assay method may include purifying and/or isolating a test compound and/or substance of interest from a mixture or extract, i.e. reducing the content of at least one component of the mixture or extract, e.g. a component with which the test substance is naturally associated. The screening or assay method may include determining the ability of one or more fractions of a test mixture or extract to bind to a polypeptide or peptide of the invention or determining the ability of one or more fractions of a test mixture or extract to bind to or affect the activity of IL-TIF/IL-22.

The purifying and/or isolation may employ any method known to those skilled in the art, for instance using an antibody molecule.

In addition to their use in purifying polypeptide chains and receptors of the invention, antibody molecules represent themselves a further class of potential modulators of receptor function.

Irrespective of the nature of the test compounds being tested in an assay method of the invention, interaction or binding between substances, e.g. an IL-22BP polypeptide and IL-TIF/IL-22, may be determined by any number of techniques available in the art, qualitative or quantitative. They include techniques such as radioimmunoassay, co-immunoprecipitation, scintillation proximity assay and ELISA methods.

Binding of one component to another may be studied by labeling either one with a detectable label and bringing it into contact with the other which may have been immobilized on a solid support. Suitable detectable labels, especially for peptidyl substances include $^{35}$S-methionine which may be incorporated into recombinantly produced peptides and polypeptides. Recombinantly produced peptides and polypeptides may also be expressed as fusion proteins containing an epitope which can be labeled with an antibody.

The polypeptide or peptide which is immobilized on a solid support may be immobilized using an antibody against that polypeptide bound to a solid support or via other technologies which are known per se. A preferred in vitro interaction may utilize a fusion peptide including glutathione-S-transferase (GST). This may be immobilized on glutathione agarose beads. In an in vitro assay format of the type described above a test modulator can be assayed by determining its ability to diminish the amount of labeled peptide or polypeptide (e.g. labeled IL-TIF/IL-22) which binds to the immobilized GST-fusion peptide (e.g. immobilized fusion peptide of GST and IL-22BP or fragment thereof). This may be determined by fractionating the glutathione-agarose beads by SDS-polyacrylamide gel electrophoresis. Alternatively, the beads may be rinsed to remove unbound peptide or polypeptide and the amount of peptide or polypeptide which has bound can be determined by counting the amount of label present in, for example, a suitable scintillation counter.

Binding or interaction of two components may also be determined using a two-hybrid assay.

For example, an IL-22BP polypeptide of the invention may be fused to a DNA binding domain such as that of the yeast transcription factor GAL4. The GAL4 transcription factor includes two functional domains. These domains are the DNA binding domain (GAL4DBD) and the GAL4 transcriptional activation domain (GAL4TAD). By fusing a first polypeptide component of the assay to one of those domains, and a second polypeptide component of the assay to the respective counterpart, a functional GAL4 transcription factor is restored only when the two polypeptides interact. Thus, interaction of these polypeptides may be measured by the use of a reporter gene linked to a GAL4 DNA binding site which is capable of activating transcription of said reporter gene.

This two hybrid assay format is described by Fields and Song, 1989, Nature 340: 245–246. It can be used in both mammalian cells and in yeast. Other combinations of DNA binding domain and transcriptional activation domain are available in the art and may be preferred, such as the LexA DNA binding domain and the VP60 transcriptional activation domain.

The precise format of any of the screening or assay methods of the present invention may be varied by those of skill in the art using routine skill and knowledge. The skilled person is well aware of the need to employ appropriate control experiments.

Performance of an assay method according to the present invention may be followed by isolation and/or manufacture and/or use of a compound, substance or molecule which tests positive for ability to modulate the relevant interaction or affect the relevant biological function or activity. Following identification of a suitable agent, it may be investigated further, and may be modified or derivatized to alter one or more properties, without abolishing its ability to modulate the relevant interaction or affect the relevant biological function. For instance, a single chain Fv antibody molecule may be reformatted into a whole antibody comprising antibody constant regions, e.g. an IgG antibody. Any peptidyl molecule may be modified by addition, substitution, insertion or deletion of one or more amino acids, or by joining of an addition moiety or protein domain. An active agent may be subject to molecular modelling in silico and one or more mimetics of the originally identified agent may be created.

Furthermore, an active agent of the invention may be manufactured and/or used in preparation, i.e. manufacture or formulation, of a composition such as a medicament, pharmaceutical composition or drug. These may be administered to individuals, as discussed.

A compound, whether a peptide, antibody, small molecule or other substance found to have the ability to affect binding between polypeptide chains of a receptor of the invention or binding of such a receptor to a ligand has therapeutic and other potential in a number of contexts. For therapeutic treatment such a compound may be used in combination with any other active substance.

Generally, such a substance identified according to the present invention and to be subsequently used is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. Thus, a composition may consist of the active ingredient obtained using the invention, and an inert carrier. Furthermore, a composition according to the present invention may include in addition to an modulator compound as disclosed, one or more other molecules of therapeutic use.

Also a part of this invention is a method for determining the presence of the receptor-like antagonist of this invention in a tissue or cell sample comprising contacting said sample with an antibody specific for said receptor-like antagonist and determining binding therebetween. Methods for determining the binding of an antibody and its antigen are well known to those of skill in the art and need not be elaborated herein.

The receptor-like binding protein of this invention may also be used to determine the presence of IL-TIF/IL-22 in a sample by, e.g., labeling said receptor-like binding protein and then contacting said sample with said receptor-like antagonist and determining binding therebetween wherein said binding is indicative of the presence of IL-TIF. Alternatively, one may determine the presence of IL-TIF/IL-22 in a sample by treating a cell line that is responsive to IL-TIF/IL-22 to two aliquots of said sample, one containing the receptor-like binding protein and one without the receptor-like binding protein, then measuring and comparing the response of said responsive cell to the two aliquots wherein a difference in response to the two aliquots is indicative of the presence of IL-TIF/IL-22. In the alternative, cells that are responsive to IL-TIF/IL-22 can be used in such assays. To elaborate, cells which show some type of response to IL-TIF/IL-22, such as increased STAT activation or acute phase reactant production, can be used to screen for presence and/or amount of IL-22BP in a sample. For example, assuming that the cell is incubated in the sample in question together with IL-TIF/IL-22, any observed change in the response, such as a decrease in STAT activation or acute phase reactant production, is indicative of IL-22 BP in said sample.

The soluble IL-TIF/IL-22 binding proteins described herein are further examples of soluble, cytokine receptors generated in vivo. See, e.g. Rose-John, et al., Biochem J. 300: 281 (1994); Femandez-Botran, et al., Adv. Immunol 63:269 (1996). Heaney, et al., Blood 87: 845 (1996). Soluble cytokine receptors compete with cell surface receptors for binding to free or unbound cytokine molecules. With the exception of IL-6R, this binding prevents cytokines from reaching the cell membrane and generating a signal. The binding is generally reversible, leading to temporary sequestration of the cytokine from membrane receptors. Soluble cytokine receptors also enhance the activity of cytokines by modifying their stability, decreasing proteolytic degradation, or reducing clearance. Such functions, i.e., as cytokine carriers in vivo, are seen to help potentiate the systemic effect of cytokines, with the antagonistic effect being pertinent to paracrine activities.

Other features of the invention will be clear to the artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule which encodes a soluble protein which binds to IL-TIF/IL-22, wherein said nucleic acid molecule encodes a protein, comprising SEQ ID NO: 11.

2. The isolated nucleic acid molecule of claim 1, comprising the nucleotide sequence of SEQ ID NO: 10.

3. An expression vector comprising the isolated nucleic acid molecule of claim 2, operably linked to a promoter.

4. A recombinant cell line or cell strain, transformed or transfected with the expression vector of claim 3.

5. A recombinant cell line or cell strain, transformed or transfected with the isolated nucleic acid molecule of claim 2.

6. An expression vector comprising the isolated nucleic acid molecule of claim 1, operably linked to a promoter.

7. A recombinant cell line or cell strain, transformed or transfected with the expression vector of claim 6.

8. A recombinant cell line or cell strain, transformed or transfected with the isolated nucleic acid molecule of claim 1.

* * * * *

UNITED STATES PATENT AND TRADEMARK OFFICE

CERTIFICATE OF CORRECTION

PATENT NO. : 7,094,570 B2
APPLICATION NO. : 10/385586
DATED : August 22, 2006
INVENTOR(S) : Jean-Christophe Renauld et al.

It is certified that error appears in the above-identified patent and that said Letters Patent is hereby corrected as shown below:

On the title page after item "(22)," please insert as new items (63) and (60):

--Related U.S. Application Data

(63) Continuation of application No. PCT/US01/29576, filed on Sep. 21, 2001, which is a continuation-in-part of application No. 09/919,162, filed Jul. 31, 2001, allowed.

(60) Provisional application No. 60/245,495, filed on Nov. 3, 2000, and provisional application No. 60/234,583, filed Sep. 22, 2000.--

At column 1, lines 9-15, please replace the paragraph with the following related application information:

--This application is a continuation of international application PCT/US01/29576, filed September 21, 2001, which is a continuation-in-part of application No. 09/919,162, filed July 31, 2001 (allowed), which claims the benefit of provisional applications 60/245,495, filed Nov. 3, 2000, and 60/234,583, filed September 22, 2000, all of which are incorporated by reference in their entirety.--

Signed and Sealed this

Twenty-eighth Day of August, 2007

JON W. DUDAS

*Director of the United States Patent and Trademark Office*

SEQUENCE LISTING

```
<160> NUMBER OF SEQ ID NOS: 11

<210> SEQ ID NO 1
<211> LENGTH: 21
<212> TYPE: DNA
<213> ORGANISM: Homo sapiens

<400> SEQUENCE: 1

agggtacaat ttcagtcccg a                                          21


<210> SEQ ID NO 2
<211> LENGTH: 21
<212> TYPE: DNA
<213> ORGANISM: Homo sapiens

<400> SEQUENCE: 2

cggcgtcatg ctccattctg a                                          21


<210> SEQ ID NO 3
<211> LENGTH: 28
<212> TYPE: DNA
<213> ORGANISM: Homo sapiens

<400> SEQUENCE: 3

tgaacagtca cactcgagac catgatgc                                   28


<210> SEQ ID NO 4
<211> LENGTH: 25
<212> TYPE: DNA
<213> ORGANISM: Homo sapiens

<400> SEQUENCE: 4

catcctgttc tcgaggagct ttaga                                      25


<210> SEQ ID NO 5
<211> LENGTH: 2271
<212> TYPE: DNA
<213> ORGANISM: Homo sapiens

<400> SEQUENCE: 5

ctgccttaaa cccgggagtg attgtctgtt tgtggatttt acagtttcct ctttggtcct     60
```

-continued

```
gagctggtta aaaggaacac tggttgcctg aacagtcaca cttgcaacca tgatgcctaa    120

acattgcttt ctaggcttcc tcatcagttt cttccttact ggtgtagcag gaactcagtc    180

aacgcatgag tctctgaagc ctcagagggt acaatttcag tcccgaaatt ttcacaacat    240

tttgcaatgg cagcctggga gggcacttac tggcaacagc agtgtctatt ttgtgcagta    300

caaaatatat ggacagagac aatggaaaaa taaagaagac tgttggggta ctcaagaact    360

ctcttgtgac cttaccagtg aaacctcaga catacaggaa ccttattacg ggagggtgag    420

ggcggcctcg gctgggagct actcagaatg gagcatgacg ccgcggttca ctccctggtg    480

ggaaacaaaa atagatcctc cagtcatgaa tataacccaa gtcaatggct ctttgttggt    540

aattctccat gctccaaatt taccatatag ataccaaaag gaaaaaaatg tatctataga    600

agattactat gaactactat accgagtttt tataattaac aattcactag aaaaggagca    660

aaaggtttat gaaggggctc acagagcggt tgaaattgaa gctctaacac cacactccag    720

ctactgtgta gtggctgaaa tatatcagcc catgttagac agaagaagtc agagaagtga    780

agagagatgt gtggaaattc catgacttgt ggaatttggc attcagcaat gtggaaattc    840

taaagctccc tgagaacagg atgactcgtg tttgaaggat cttatttaaa attgtttttg    900

tattttctta aagcaatatt cactgttaca ccttggggac ttctttgttt atccattctt    960

ttatccttta tatttcattt gtaaactata tttgaacgac attccccccg aaaaattgaa   1020

atgtaaagat gaggcagaga ataaagtgtt ctatgaaatt cagaacttta tttctgaatg   1080

taacatccct aataacaacc ttcattcttc taatacagca aaataaaaat ttaacaacca   1140

aggaatagta tttaagaaaa tgttgaaata attttttttaa aatagcatta cagactgagg   1200

cggtcctgaa gcaatggttt ttcactctct tattgagcca attaaattga cattgctttg   1260

acaatttaaa acttctataa aggtgaatat ttttcataca tttctatttt atatgaatat   1320

actttttata tatttattat tattaaatat ttctacttaa tgaatcaaaa ttttgtttta   1380

aagtctactt tatgtaaata agaacaggtt ttggggaaaa aaatcttatg atttctggat   1440

tgatatctga attaaaacta tcaacaacaa ggaagtctgc tctgtacaat tgtccctcat   1500

ttaaaagata tattaagctt ttcttttctg tttgtttttg ttttgtttag tttttaatcc   1560

tgtcttagaa gaacttatct ttattctcaa aattaaatgt aatttttttta gtgacaaaga   1620

agaaaggaaa cctcattact caatccttct ggccaagagt gtcttgcttg tggcgccttc   1680

ctcatctcta tataggagga tcccatgaat gatggtttat tgggaactgc tggggtcgac   1740

cccatacaga gaactcagct tgaagctgga agcacacagt gggtagcagg agaaggaccg   1800

gtgttggtag gtgcctacag agactataga gctagacaaa gccctccaaa ctggcccctc   1860

ctgctcactg cctctcctga gtagaaatct ggtgacctaa ggctcagtgt ggtcaacaga   1920

aagctgcctt cttcacttga ggctaagtct tcatatatgt ttaaggttgt ctttctagtg   1980

aggagataca tatcagagaa catttgtaca attccccatg aaaattgctc caaagttgat   2040

aacaatatag tcggtgcttc tagttatatg caagtactca gtgataaatg gattaaaaaa   2100

tattcagaaa tgtattgggg ggtggaggag aataagaggc agagcaagag ctagagaatt   2160

ggtttccttg cttccctgta tgctcagaaa acattgattt gagcatagac gcagagactg   2220

aaaaaaaaat ttactttgat ctctgttttt gaattcttat tatttatatt t            2271
```

<210> SEQ ID NO 6
<211> LENGTH: 231
<212> TYPE: PRT
<213> ORGANISM: Homo sapiens

<400> SEQUENCE: 6

```
Met Met Pro Lys His Cys Phe Leu Gly Phe Leu Ile Ser Phe Phe Leu
                5                  10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230
```

<210> SEQ ID NO 7
<211> LENGTH: 37
<212> TYPE: DNA
<213> ORGANISM: Homo sapiens

<400> SEQUENCE: 7

```
ccaacttcca tgatcaatgg aatttccaca catctct                            37
```

<210> SEQ ID NO 8
<211> LENGTH: 33
<212> TYPE: DNA
<213> ORGANISM: Homo sapiens

<400> SEQUENCE: 8

```
aagactgagt tgatcaagag aatcgagcct aga                                33
```

<210> SEQ ID NO 9
<211> LENGTH: 27
<212> TYPE: DNA
<213> ORGANISM: Homo sapiens

<400> SEQUENCE: 9

```
aatgtctaga tgctgttctc atttacc                                       27
```

-continued

<210> SEQ ID NO 10
<211> LENGTH: 2367
<212> TYPE: DNA
<213> ORGANISM: Homo sapiens

<400> SEQUENCE: 10

```
ctgccttaaa cccgggagtg attgtctgtt tgtggatttt acagtttcct ctttggtcct     60

gagctggtta aaaggaacac tggttgcctg aacagtcaca cttgcaacca tgatgcctaa    120

acattgcttt ctaggcttcc tcatcagttt cttccttact ggtgtagcag gaactcagtc    180

aacgcatgag tctctgaagc ctcagagggt acaatttcag tcccgaaatt ttcacaacat    240

tttgcaatgg cagcctggga gggcacttac tggcaacagc agtgtctatt ttgtgcagta    300

caaaatcatg ttctcatgca gcatgaaaag ctctcaccag agccaagtgg atgcttggca    360

gcacatttct tgtaacttcc caggctgcag aacattggct aaatatggac agagacaatg    420

gaaaaataaa gaagactgtt ggggtactca agaactctct tgtgacctta ccagtgaaac    480

ctcagacata caggaacctt attacgggag ggtgagggcg gcctcggctg ggagctactc    540

agaatggagc atgacgccgc ggttcactcc ctggtgggaa acaaaaatag atcctccagt    600

catgaatata acccaagtca atggctcttt gttggtaatt ctccatgctc caaatttacc    660

atatagatac caaaaggaaa aaaatgtatc tatagaagat tactatgaac tactataccg    720

agtttttata attaacaatt cactagaaaa ggagcaaaag gtttatgaag ggctcacag    780

agcggttgaa attgaagctc taacaccaca ctccagctac tgtgtagtgg ctgaaatata    840

tcagcccatg ttagacagaa gaagtcagag aagtgaagag agatgtgtgg aaattccatg    900

acttgtggaa tttggcattc agcaatgtgg aaattctaaa gctccctgag aacaggatga    960

ctcgtgtttg aaggatctta tttaaaattg tttttgtatt ttcttaaagc aatattcact   1020

gttacacctt ggggacttct ttgtttatcc attcttttat cctttatatt tcatttgtaa   1080

actatatttg aacgacattc cccccgaaaa attgaaatgt aaagatgagg cagagaataa   1140

agtgttctat gaaattcaga actttatttc tgaatgtaac atccctaata acaaccttca   1200

ttcttctaat acagcaaaat aaaaatttaa caaccaagga atagtattta agaaaatgtt   1260

gaaataattt ttttaaaata gcattacaga ctgaggcggt cctgaagcaa tggtttttca   1320

ctctcttatt gagccaatta aattgacatt gctttgacaa tttaaaactt ctataaaggt   1380

gaatattttt catacatttc tattttatat gaatatactt tttatatatt tattattatt   1440

aaatatttct acttaatgaa tcaaaatttt gttttaaagt ctactttatg taaataagaa   1500

caggttttgg ggaaaaaaat cttatgattt ctggattgat atctgaatta aaactatcaa   1560

caacaaggaa gtctgctctg tacaattgtc cctcatttaa aagatatatt aagcttttct   1620

tttctgtttg tttttgtttt gtttagtttt taatcctgtc ttagaagaac ttatctttat   1680

tctcaaaatt aaatgtaatt tttttagtga caaagaagaa aggaaacctc attactcaat   1740

ccttctggcc aagagtgtct tgcttgtggc gccttcctca tctctatata ggaggatccc   1800

atgaatgatg gtttattggg aactgctggg gtcgacccca tacagagaac tcagcttgaa   1860

gctggaagca cacagtgggt agcaggagaa ggaccggtgt tggtaggtgc ctacagagac   1920

tatagagcta gacaaagccc tccaaactgg cccctcctgc tcactgcctc tcctgagtag   1980

aaatctggtg acctaaggct cagtgtggtc aacagaaagc tgccttcttc acttgaggct   2040

aagtcttcat atatgtttaa ggttgtcttt ctagtgagga gatacatatc agagaacatt   2100

tgtacaattc cccatgaaaa ttgctccaaa gttgataaca atatagtcgg tgcttctagt   2160
```

-continued tatatgcaag tactcagtga taaatggatt aaaaaatatt cagaaatgta ttggggggtg 2220
gaggagaata agaggcagag caagagctag agaattggtt tccttgcttc cctgtatgct 2280
cagaaaacat tgatttgagc atagacgcag agactgaaaa aaaaatttac tttgatctct 2340
gtttttgaat tcttattatt tatattt 2367

<210> SEQ ID NO 11
<211> LENGTH: 263
<212> TYPE: PRT
<213> ORGANISM: Homo sapiens

<400> SEQUENCE: 11

Met Met Pro Lys His Cys Phe Leu Gly Phe Leu Ile Ser Phe Phe Leu
1 5 10 15

Thr Gly Val Ala Gly Thr Gln Ser Thr His Glu Ser Leu Lys Pro Gln
20 25 30

Arg Val Gln Phe Gln Ser Arg Asn Phe His Asn Ile Leu Gln Trp Gln
35 40 45

Pro Gly Arg Ala Leu Thr Gly Asn Ser Ser Val Tyr Phe Val Gln Tyr
50 55 60

Lys Ile Met Phe Ser Cys Ser Met Lys Ser Ser His Gln Ser Gln Val
65 70 75 80

Asp Ala Trp Gln His Ile Ser Cys Asn Phe Pro Gly Cys Arg Thr Leu
85 90 95

Ala Lys Tyr Gly Gln Arg Gln Trp Lys Asn Lys Glu Asp Cys Trp Gly
100 105 110

Thr Gln Glu Leu Ser Cys Asp Leu Thr Ser Glu Thr Ser Asp Ile Gln
115 120 125

Glu Pro Tyr Tyr Gly Arg Val Arg Ala Ala Ser Ala Gly Ser Tyr Ser
130 135 140

Glu Trp Ser Met Thr Pro Arg Phe Thr Pro Trp Trp Glu Thr Lys Ile
145 150 155 160

Asp Pro Pro Val Met Asn Ile Thr Gln Val Asn Gly Ser Leu Leu Val
165 170 175

Ile Leu His Ala Pro Asn Leu Pro Tyr Arg Tyr Gln Lys Glu Lys Asn
180 185 190

Val Ser Ile Glu Asp Tyr Tyr Glu Leu Leu Tyr Arg Val Phe Ile Ile
195 200 205

Asn Asn Ser Leu Glu Lys Glu Gln Lys Val Tyr Glu Gly Ala His Arg
210 215 220

Ala Val Glu Ile Glu Ala Leu Thr Pro His Ser Ser Tyr Cys Val Val
225 230 235 240

Ala Glu Ile Tyr Gln Pro Met Leu Asp Arg Arg Ser Gln Arg Ser Glu
245 250 255

Glu Arg Cys Val Glu Ile Pro
260